(12) United States Patent
Guidotti et al.

(10) Patent No.: US 7,468,451 B2
(45) Date of Patent: Dec. 23, 2008

(54) PROCESS FOR THE PRODUCTION OF HALIDE METALLOCENE COMPOUNDS

(75) Inventors: Simona Guidotti, Altedo-Malalbergo (IT); Davide Balboni, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 614 days.

(21) Appl. No.: 10/555,434

(22) PCT Filed: Apr. 29, 2004

(86) PCT No.: PCT/EP2004/004525

§ 371 (c)(1),
(2), (4) Date: Nov. 3, 2005

(87) PCT Pub. No.: WO2004/099225

PCT Pub. Date: Nov. 18, 2004

(65) Prior Publication Data

US 2007/0043228 A1    Feb. 22, 2007

Related U.S. Application Data

(60) Provisional application No. 60/469,191, filed on May 9, 2003.

(30) Foreign Application Priority Data

May 8, 2003    (EP) ................... 03101268

(51) Int. Cl.
*C07F 17/00*    (2006.01)
*C07F 9/02*    (2006.01)
*C07F 7/00*    (2006.01)

(52) U.S. Cl. .................... 556/11; 556/12; 556/19; 556/52; 556/53

(58) Field of Classification Search ............. 556/11, 556/12, 19, 52, 53
See application file for complete search history.

(56) References Cited

U.S. PATENT DOCUMENTS

| 6,869,903 | B2 * | 3/2005 | Matsunaga ............... 502/152 |
| 6,987,196 | B2 * | 1/2006 | Resconi et al. ............ 556/11 |
| 7,002,031 | B2 | 2/2006 | Resconi et al. ............ 556/11 |
| 2003/0008984 | A1 | 1/2003 | Kratzer et al. ............ 526/127 |
| 2003/0013913 | A1 | 1/2003 | Schottek et al. ............ 564/8 |

FOREIGN PATENT DOCUMENTS

| DE | 19962814 | 6/2001 |
| DE | 19962910 | 7/2001 |
| EP | 0129368 | 12/1984 |
| WO | 9102012 | 2/1991 |
| WO | 9200333 | 1/1992 |
| WO | 9519984 | 7/1995 |
| WO | 9936427 | 7/1999 |
| WO | 0075151 | 12/2000 |
| WO | 0162764 | 8/2001 |
| WO | 02083699 | 10/2002 |
| WO | 03057705 | 7/2003 |
| WO | 04037840 | 5/2004 |

OTHER PUBLICATIONS

F. Wild et al., "*ansa*-Metallocene Derivatives; VII. Synthesis and Crystal Structure of a Chiral *ansa*-Zirconocene Derviative with Ethylene-Bridged Tetrahydroindenyl Ligands,"*Journal of Organometallic Chemistry*, vol. 288, p. 63-67 (1985).

I. M. Lee et al., "Electronic Effects in Ziegler-Natta Polymerization of Propylene and Ethylene Using Soluble Metallocene Catalysts," *Organometallics*, vol. 11, p. 2115-2122 (1992).

* cited by examiner

*Primary Examiner*—Porfirio Nazario Gonzalez
(74) *Attorney, Agent, or Firm*—Jarrod N. Raphael

(57) ABSTRACT

Process for preparing halide metallocene compounds comprising the step of reacting the dialkyl derivative with a halogenating agent of formula $R^3_x TL_w$ wherein: L is chlorine, iodine or bromine; $R^3$ is hydrogen or a hydrocarbon group; T is a metal of groups 2-14 of the periodic table of the elements; and x is $\geq 1$ so that x+w is equal to the oxidation state of the metal T.

13 Claims, No Drawings

PROCESS FOR THE PRODUCTION OF HALIDE METALLOCENE COMPOUNDS

The present invention relates to a process for the production of halide metallocene compounds in high purity and in high yields.

Metallocene compounds are well known in the art as catalyst components for the polymerization of olefins. For instance, the European Patent Application EP 0 129 368 discloses catalysts comprising mono- and di-cyclopentadienyl coordination complexes with a transition metal in combination with an alumoxane.

In those metallocene compounds, the central metal is coordinated with one or more π-bonded ligands, usually cyclopentadienyl moieties, and with one or more sigma-bonded ligands. The latter are usually halogen, preferably chlorine. In the usual process for preparing dihalide metallocene compounds the lithium salts of the ligands are contacted with a tetrahalide of the metal. This process generates LiCl as a by-product that is difficult to separate because of the low solubility of the dihalide metallocene compounds in the usual solvents, and often the yield of the process is not satisfactory.

For instance, F. Wild et al. (*J. Organomet. Chem.*, 288:63-67, 1985) describe the synthesis of chiral ansa-zirconocene derivatives with ethylene-bridged ligands. In particular, it is reported the preparation of ethylene-bis(1-indenyl)zirconium dichloride by reaction of the dilithium salt of bis(1-indenyl)ethane with $ZrCl_4$, in a yield of about 35%. Better results have been obtained by I. M. Lee et al. (*Organometallics,* 11:2115-2122, 1992), who prepared ethylene-bis(1-indenyl)zirconium dichloride in a yield of 52%. Another example can be found in Polyhedron 1990, 9, 301 wherein it is reported the synthesis of bis(indenyl)zirconium dichloride starting from indene and zirconium tetrachloride with a final yield of 58%.

In WO 02/083699, dialkyl metallocene compounds are treated with a halogenating agent such as HCl, transition metal halides, $BCl_3$ and the like in order to obtain a monohalide or dihalide compound in high yields. It has now been found that, by using different halogenating agents, the yields of that process can be further increased.

Thus, according to a first aspect, the present invention provides a process for preparing halide metallocene compounds of formula (I):

$$(Cp)(ZR^1_m)_n(A)_rML'_yL'_t \qquad (I)$$

wherein $(ZR^1_m)_n$ is a divalent group bridging the Cp and A moieties; Z being C, Si, Ge, N or P, and the $R^1$ groups, equal to or different from each other, being hydrogen or linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl groups, optionally containing one or more heteroatoms belonging to groups 13-17 of the Periodic Table of the Elements, or two $R^1$ can form an aliphatic or aromatic $C_4$-$C_7$ ring that can bear substituents;

Cp is an unsubstituted or substituted cyclopentadienyl group, optionally condensed to one or more unsubstituted or substituted, saturated, unsaturated or aromatic rings, containing from 4 to 6 carbon atoms, optionally containing one or more heteroatoms belonging to groups 13-17 of the Periodic Table of the Elements;

A is O, S, $NR^2$ or $PR^1$, $R^2$ being hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl, or A has the same meaning of Cp;

M is zirconium, titanium or hafnium;

the L substituents, equal to or different from each other, preferably equal, are chlorine, bromine, iodine, preferably chlorine;

L' is hydrogen, or a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl group, optionally containing one or more Si or Ge atoms; preferably L' is methyl, ethyl, n-butyl, sec-butyl, phenyl, benzyl or —$CH_2Si(CH_3)_3$; more preferably L' is methyl;

m is 1 or 2 depending on the oxidation state of Z, more specifically it is 1 when Z is N or P, and it is 2 when Z is C, Si or Ge;

n is 0, 1, 2, 3 or 4, preferably it is 0, 1 or 2; being 0 when r is 0 or 2;

r is 0, 1 or 2, preferably being 0 or 1; more preferably r is 1;

y is 1, 2, or 3; preferably y is 2; and t is 0, 1 or 2, preferably t is 0; the sum of y+t being equal to the oxidation state of the metal M minus 1+r;

said process comprising contacting a compound of formula (II):

$$(Cp)(ZR^1_m)_n(A)_rML'_p \qquad (II)$$

wherein

Cp, Z, $R^1$, A, M, L', m, r, and n have the same meaning as above; and p is equal to the oxidation state of the metal M minus 1+r; preferably p is 2;

with at least p-t equivalents, with respect to the metal M of the compound of formula (II), of an halogenating agent of formula (III):

$$R^3_xTL_w \qquad (II)$$

or an adduct containing the compound of formula (III);

wherein:

L has the same meaning as above;

$R^3$ is hydrogen, or a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl group; preferably $R^3$ is methyl, ethyl, n-propyl, isopropyl, n-butyl, isobutyl, phenyl or benzyl; more preferably $R^3$ is methyl, ethyl, n-propyl, isopropyl, n-butyl or isobutyl;

T is a metal of groups 2-14 of the periodic table of the elements; preferably T is a metal of groups 11-14 of the periodic table of the elements; more preferably T is aluminum, zinc, tin, germanium or copper;

x is $\geq 1$ and w is $\geq 1$ so that x+w is equal to the oxidation state of the metal T; preferably x is 1.

The compounds of formula (II) can be prepared according to known methods, as described, for example, in WO 99/36427, WO 00/75151 and WO 03/057705.

The process of the present invention can be also the last step of a "one pot" process in which the compound of formula (I) is prepared according to WO 99/36427, WO 00/75151 and WO 03/057705 and then, without being isolated, said compound is halogenated according to the process of the present invention.

Therefore a further object of the present invention is a process for preparing halide metallocene compounds of formula (I):

$$(Cp)(ZR^1_m)_n(A)_rML'_yL'_t \qquad (I)$$

wherein Cp, Z, $R^1$, m, n, A, r, M, L, L', t and y have the same meaning as above;

comprising the following steps:

a) reacting a ligand of formula $(Y\text{-}Cp)(ZR^1_m)_n(A\text{-}Y)_r$ or when n is 0 a mixture of ligands Y-Cp and r(A-Y) with an amount EQ of a compound of formula $L'_jB$ or L'MgL''' such that $EQ \geq 1+r$ molar equivalents with respect to Cp, preferably $1+r \leq EQ \leq 4+r$ wherein Cp, A, Z, $R^1$, m, n, r, and L' have the meaning reported above; L''' is selected from the group consisting of chlorine, bromine, iodine; the groups Y, the same or different from each other, are suitable leaving groups; Mg is magnesium; B is an alkaline or alkaline-earth metal; and j is 1 or 2, j being equal to 1 when B is an alkali metal, and j being equal to 2 when B is an alkaline-earth metal;

b) reacting the product obtained from previous step with at least 1 molar equivalent with respect to Cp of a compound of formula ML''$_4$, wherein M have the meaning reported above, L'' is selected from the group consisting of chlorine, bromine, iodine;

c) optionally purifying the mixture and separating the meso and the rac forms; and d) reacting the mixture obtained from the previous steps with at least y equivalents with respect to the metal M of an halogenating agent of formula (III):

$$R^3_x TL_w \quad (III)$$

wherein $R^3$, T, L, x and w have been described above.

According to a preferred embodiment of the present invention, all the reactions of the above processes are carried out in an aprotic solvent, either polar or apolar. Said aprotic solvent is preferably an aromatic or aliphatic hydrocarbon, optionally halogenated, or an ether, more preferably it is selected from the group consisting of benzene, toluene, pentane, hexane, heptane, cyclohexane, dichloromethane, chlorobenzene, diethylether, tetrahydrofuran or mixtures thereof.

The amount of the halogenating agent to be used depends from the type of compound. For the purpose of the present invention the term "equivalent of an halogenating agent" is referred to the equivalents of active groups L i.e. the groups L in the compound of formula (III) that are able to react. The number of active group L can be equal to or less than w. In any case excess of halogenating agent can also be used.

The Y leaving group is preferably hydrogen or a trialkylsilyl group.

The ML''$_4$ reactant is preferably selected from the group consisting of $TiCl_4$, $ZrCl_4$, $HfCl_4$. It can be used even in the form of a stabilized derivative, such as an etherate complex of ML''$_4$, easily available on the market.

The compounds $L'_jB$ and L'''MgL' are alkylating agents. Preferably L' is selected from the group consisting of methyl, ethyl, n-butyl, sec-butyl, phenyl, benzyl and —$CH_2Si(CH_3)_3$. More preferably L' is methyl or butyl.

In the compound $L'_jB$, B is an alkali or alkaline-earth metal, preferably Li or Mg; j can be 1 or 2, as already reported.

The compound L'''MgL' is a Grignard reagent, wherein Mg is magnesium and L''' and L' have the meanings reported above. L''' is preferably bromine or iodine.

According to a preferred embodiment of the process of the invention, said alkylating agent is the compound of formula $L'_jB$, more preferably butyl lithium or methyllithium.

Preferably step a) of the above process is carried out in two substeps:

a-1) reacting, at a temperature of between −10° C. and 70° C., a ligand of formula $(Y\text{-}Cp)(ZR^1_m)_n(A\text{-}Y)_r$ or when n is 0 a mixture of ligands Y-Cp and r(A-Y) with an amount EQ of a compound of formula $L'_jB$ or L'MgL''' such that EQ is about 1+r molar equivalents with respect to Cp; and a-2) after the reaction has been completed, i.e. in a time ranging from 1 minute to 6 hours, preferably from 20 minutes to 5 hours, more preferably from 40 minutes to 5 hours, adding a further amount EQ of a compound of formula $L'_jB$ or L'MgL''' such that $1+r \leq EQ \leq 2+r$.

For the purpose of the present invention the term "about" means that the quantity to which said term is referred can vary from −15% to +15%.

The alkylating agents used in substeps a-1) and a-2) can be the same or different. For example, butyllithium or sodium hydride can be used in step a-1) and methyl lithium can be used in step a-2). This gives rise to the advantage that it is possible to use stronger and sometimes less expensive reagents in step a-1) without influencing the choice of the substituents L' in step a-2).

Preferably in the processes for preparing compounds of formula (I), in step (a) or substeps a-1) and a-2) the alkylating agent is preferably added in the form of a solution in one of the above mentioned aprotic solvents, preferably dropwise.

Before the reaction with ML''$_4$, in step (b), the mixture obtained from step (a) is preferably heated at a temperature comprised between 0° C. and 80° C., and more preferably between 20° C. and 74° C. Afterwards the compound ML''$_4$ is quickly added to the slurry in the form of a solution or a slurry in one of the above mentioned aprotic solvents, preferably pentane, hexane, heptane or toluene. The reaction mixture is then allowed to react for a period ranging from 10 minutes to 36 hours, and more preferably from 1 hour to 18 hours.

In the halogenating step d) in which the compound of formula (III) is added, the temperature ranges from −50° C. to +150° C., preferably from 0° C. to 100° C., more preferably from 20° C. to 75° C. The halogenating agent is generally added dropwise and then the reaction mixture is preferably allowed to react, under stirring, for a period ranging from 1 to 6 hours, more preferably from 2 to 3 hours, at a temperature comprised between −10° C. and +80° C. Non limiting examples of halogenating agents of formula (III) are:

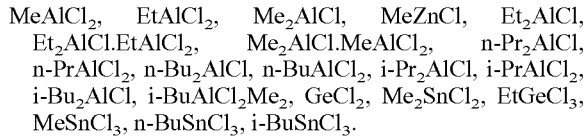

$MeAlCl_2$, $EtAlCl_2$, $Me_2AlCl$, $MeZnCl$, $Et_2AlCl$, $Et_2AlCl.EtAlCl_2$, $Me_2AlCl.MeAlCl_2$, $n\text{-}Pr_2AlCl$, $n\text{-}PrAlCl_2$, $n\text{-}Bu_2AlCl$, $n\text{-}BuAlCl_2$, $i\text{-}Pr_2AlCl$, $i\text{-}PrAlCl_2$, $i\text{-}Bu_2AlCl$, $i\text{-}BuAlCl_2Me_2$, $GeCl_2$, $Me_2SnCl_2$, $EtGeCl_3$, $MeSnCl_3$, $n\text{-}BuSnCl_3$, $i\text{-}BuSnCl_3$.

wherein Me is a methyl radical, Et is an ethyl radical, n-Pr is a normal propyl radical, i-Pr is a isopropyl radical, n-Bu is a normal butyl radical, i-Bu is an isobutyl radical.

The thus obtained metallocene compounds of formula (I) can be isolated according to the common procedures known in the state of the art.

In the optional step (c) the purification of the reaction mixture is preferably carried out by simply filtering the solution in order to remove the salts. Also other systems of purification can be used, for example a suitable solvent can be added in order to precipitate the undesired by products with subsequently filtration. In these steps it is also possible to separate (when present) the racemic and the meso form by using methods known in the art. For example, by using suitable solvents it is possible to precipitate one form with subsequently filtration. All the operations are carried out in inert atmosphere.

In the metallocenes of formula (I) and (II), the divalent bridge $(ZR^1{}_m)_n$ is preferably selected from the group consisting of $CR^1{}_2$, $(CR^1{}_2)_2$, $(CR^1{}_2)_3$, $SiR^1{}_2$, $GeR^1{}_2$, $NR^1$ and $PR^1$, $R^1$ having the meaning reported above. More preferably, said divalent bridge is $Si(CH_3)_2$, $SiPh_2$, $CH_2$, $(CH_2)_2$, $(CH_2)_3$ or $C(CH_3)_2$.

The variable m is 1 or 2; the variable n ranges from 0 to 4 preferably is 1 or 2, when n>1, the atoms Z can be the same or different from each other, such as in divalent bridges —$CH_2$—O—, —$CH_2$—S— and —$CH_2$—$Si(CH_3)_2$—. When n=0 and r=1, A can have only the meaning of Cp.

In the metallocenes of formula (I), the ligand Cp, which is π-bonded to said metal M, is preferably selected from the group consisting of cyclopentadienyl, mono-, di-, tri- and tetra-methyl cyclopentadienyl; 4-tertbutyl-cyclopentadienyl; 4-adamantyl-cyclopentadienyl; indenyl; mono-, di-, tri- and tetra-methyl indenyl; 2-methyl-4-phenyl indenyl, in which the phenyl can be alkyl substituted; 2-isopropyl-4-phenyl indenyl, in which the phenyl can be alkyl substituted; 4,5,6,7-tetrahydroindenyl fluorenyl; 5,10-dihydroindeno[1,2-b]indol-10-yl; N-methyl- or N-phenyl-5,10-dihydroindeno[1,2-b]indol-10-yl; 5,6-dihydroindeno[2,1-b]indol-6-yl; N-methyl-or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl and 2,5-dimethyl-cyclopenta[1,2-b:4,3-b']-dithiophene.

The group A has preferably the same meaning of Cp, or it is N-methyl, N-ethyl, N-isopropyl, N-butyl, N-phenyl, N-benzyl, N-cyclohexyl and N-cyclododecyl.

More preferably the group Cp is a moiety of formula (IV):

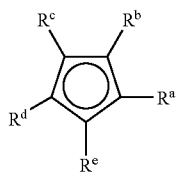

(IV)

wherein
$R^a$, $R^b$, $R^c$, $R^d$ and $R^e$, equal to or different from each other, are hydrogen atoms or linear or branched, saturated or unsaturated $C_1$-$C_{40}$-alkyl, $C_3$-$C_{40}$-cycloalkyl, $C_6$-$C_{40}$-aryl, $C_7$-$C_{40}$-alkylaryl or $C_7$-$C_{40}$-arylalkyl radicals, optionally containing heteroatoms belonging to groups 13-17 of the Periodic Table of the Elements; two vicinal $R^a$, $R^b$, $R^c$, $R^d$ and $R^e$ can also form one or more condensed 5 or 6 membered saturated or unsaturated rings optionally containing heteroatoms belonging to groups 13-16 of the Periodic Table of the Elements, said rings can bear $C_1$-$C_{20}$ alkyl or $C_6$-$C_{20}$ aryl arylalkyl or alkylaryl substituents; $R^e$ can also be a single bond that links the moiety of formula (IV) to the bridging group $(ZR^1{}_m)_n$ The metallocene compounds of formula (I) are preferably silicon-bridged metallocene compounds of formula (V):

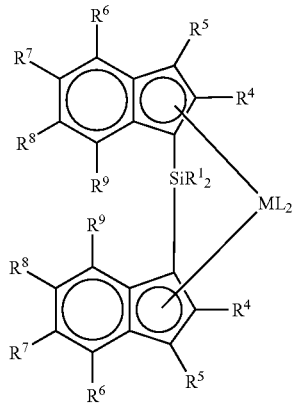

(V)

wherein:
M, L and $R^1$ have the meaning reported above;
$R^4$, equal to or different from each other, is a hydrogen atom or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements;
$R^5$, $R^6$, $R^7$, $R^8$ and $R^9$, equal to or different from each other, are hydrogen atoms or linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radicals, optionally containing heteroatoms belonging to groups 13-17 of the Periodic Table of the Elements; two vicinal $R^5$, $R^6$, $R^7$, $R^8$ and $R^9$ can also form one or more condensed 5 or 6 membered saturated or unsaturated rings optionally containing heteroatoms belonging to groups 13-16 of the Periodic Table of the Elements, said rings can bear $C_1$-$C_{40}$ alkyl substituents;
Preferably $R^4$, equal to or different from each other, is a $C_1$-$C_{20}$-alkyl radical; more preferably the two $R^4$ moieties, equal to or different from each other, are methyl ethyl or isopropyl radicals;
$R^6$ is preferably a $C_1$-$C_{20}$-alkyl, $C_6$-$C_{20}$-aryl or $C_7$-$C_{20}$-arylalkyl radicals; more preferably $R^6$ is a phenyl or a 4-$C_1$-$C_{10}$ alkyl substituted phenyl radical such as 4-tertbutyl-phenyl radical.

Non limiting examples of metallocene compounds of formula (I) are the racemic and the meso form (when present) of the following compounds:
bis(cyclopentadienyl)zirconium dichloride;
bis(indenyl)zirconium dichloride;
bis(tetrahydroindenyl)zirconium dichloride;
bis(fluorenyl)zirconium dichloride;
dimethylsilanediylbis(indenyl)zirconium dichloride,
dimethylsilanediylbis(2-methyl-4-phenylindenyl)zirconium dichloride,
dimethylsilanediylbis(4-naphthylindenyl)zirconium dichloride,
dimethylsilanediylbis(2-methylindenyl)zirconium dichloride,
dimethylsilanediylbis(2-methyl-(4-t-butyl-phenyl)indenyl) zirconium dichloride, dimethylsilanediyl(2-methyl-(4-t-butyl-phenyl)indenyl)(2-isopropyl-(4-t-butyl-phenyl)indenyl)zirconium dichloride,
dimethylsilanediylbis(2-methyl-4-isopropylindenyl)zirconium dichloride,
dimethylsilanediylbis(2,4-dimethylindenyl)zirconium dichloride,
dimethylsilanediylbis(2-methyl-4,5-benzoindenyl)zirconium dichloride,
dimethylsilanediylbis(2,4,7-trimethylindenyl)zirconium dichloride,
dimethylsilanediylbis(2,4,6-trimethylindenyl)zirconium dichloride,
dimethylsilanediylbis(2,5,6-trimethylindenyl)zirconium dichloride,
methyl(phenyl)silanediylbis(2-methyl-4,6-diisopropylindenyl)-zirconium dichloride,
methyl(phenyl)silanediylbis(2-methyl-4-isopropylindenyl)-zirconium dichloride,
1,3-propylenebis(indenyl)zirconium dichloride,
1,3-propylenebis(4,7-dimethylindenyl)zirconium dichloride,
1,3-propylenebis(2-methyl-4-phenylindenyl)zirconium dichloride,
1,3-propylenebis(2-methyl-4,6-diisopropylindenyl)zirconium dichloride,
1,3-propylenebis(2-methyl-4,5-benzoindenyl)zirconium dichloride,
1,2-ethylenebis(indenyl)zirconium dichloride,
1,2-ethylenebis(4,7-dimethylindenyl)zirconium dichloride,
1,2-ethylenebis(2-methyl-4-phenylindenyl)zirconium dichloride,
1,4-butanediylbis(2-methyl-4-phenylindenyl)zirconium dichloride,
1,2-ethylenebis(2-methyl-4,6-diisopropylindenyl)zirconium dichloride,
1,4-butanediylbis(2-methyl-4-isopropylindenyl)zirconium dichloride,
1,4-butanediylbis(2-methyl-4,5-benzoindenyl)zirconium dichloride,
1,2-ethylenebis(2-methyl-4,5-benzoindenyl)zirconium dichloride,
[4-($\eta^5$-cyclopentadienyl)-4,6,6-trimethyl($\eta^5$-4,5-tetrahydropentalene)]zirconium dichloride,
[4-($\eta^5$-3'-trimethylsilylcyclopentadienyl)-4,6,6-trimethyl($\eta^5$-4,5-tetrahydropentalene)]zirconium dichloride,
(tert-butylamido)(tetramethyl-$\eta^5$-cyclopentadienyl)-1,2-ethane-titanium dichloride,
(methylamido)(tetramethyl-$\eta^5$-cyclopentadienyl)dimethylsilyl-titanium dichloride,
(methylamido)(tetramethyl-$\eta^5$-cyclopentadienyl)-1,2-ethanediyl-titanium dichloride,
(tertbutylamido)-(2,4-dimethyl-2,4-pentadien-1-yl)dimethylsilyl-titanium dichloride,
bis(1,3-dimethylcyclopentadienyl)zirconium dichloride,
methylene(3-methyl-cyclopentadienyl)-7-(2,5-dimethylcyclopentadienyl-[1,2-b:4,3-b']dithiophene)zirconium dichloride;
methylene(3-isopropyl-cyclopentadienyl)-7-(2,5-dimethylcyclopentadienyl-[1,2-b:4,3-b']dithiophene)zirconium dichloride;
methylene(2,4-dimethyl-cyclopentadienyl)-7-(2,5-dimethylcyclopentadienyl-[1,2-b:4,3-b']dithiophene)zirconium dichloride;
methylene(2,3,5-trimethyl-cyclopentadienyl)-7-(2,5-dimethylcyclopentadienyl-[1,2-b:4,3-b']dithiophene)zirconium dichloride;
methylene-1-(indenyl)-7-(2,5-dimethylcyclopentadienyl-[1,2-b:4,3-b']dithiophene)zirconium dichloride;
methylene-1-(indenyl)-7-(2,5-ditrimethylsilylcyclopentadienyl-[1,2-b:4,3-b']dithiophene)zirconium dichloride;
methylene-1-(3-isopropyl-indenyl)-7-(2,5-dimethylcyclopentadienyl-[1,2-b:4,3-b']dithiophene)zirconium dichloride;
methylene-1-(2-methyl-indenyl)-7-(2,5-dimethylcyclopentadienyl-[1,2-b:4,3-b']dithiophene)zirconium dichloride;
methylene-1-(tetrahydroindenyl)-7-(2,5-dimethylcyclopentadienyl-[1,2-b:4,3-b']dithiophene)zirconium dichloride;
methylene(2,4-dimethyl-cyclopentadienyl)-7-(2,5-dimethylcyclopentadienyl-[1,2-b:4,3-b']dioxazol)zirconium dichloride;
methylene(2,3,5-trimethyl-cyclopentadienyl)-7-(2,5-dimethylcyclopentadienyl-[1,2-b:4,3-b']dioxazol)zirconium dichloride;
methylene-1-(indenyl)-7-(2,5-dimethylcyclopentadienyl-[1,2-b:4,3-b']dioxazol)zirconium dichloride;
isopropylidene(3-methyl-cyclopentadienyl)-7-(2,5-dimethylcyclopentadienyl-[1,2-b:4,3-b']dithiophene)zirconium dichloride;
isopropylidene(2,4-dimethyl-cyclopentadienyl)-7-(2,5-dimethylcyclopentadienyl-[1,2-b:4,3-b']dithiophene)zirconium dichloride;
isopropylidene(2,4-diethyl-cyclopentadienyl)-7-(2,5-dimethylcyclopentadienyl-[1,2-b:4,3-b']dithiophene)zirconium dichloride;
isopropylidene(2,3,5-trimethyl-cyclopentadienyl)-7-(2,5-dimethylcyclopentadienyl-[1,2-b:4,3-b']dithiophene)zirconium dichloride;
isopropylidene-1-(indenyl)-7-(2,5-dimethylcyclopentadienyl-[1,2-b:4,3-b']dithiophene)zirconium dichloride;
isopropylidene-1-(2-methyl-indenyl)-7-(2,5-dimethylcyclopentadienyl-[1,2-b:4,3-b']dithiophene)zirconium dichloride;
dimethylsilandiyl-1-(2-methyl-indenyl)-7-(2,5-dimethylcyclopentadienyl-[1,2-b:4,3-b']dithiophene)hafnium dichloride;
dimethylsilanediyl(3-tert-butyl-cyclopentadienyl)(9-fluorenyl)zirconium dichloride,
dimethylsilanediyl(3-isopropyl-cyclopentadienyl)(9-fluorenyl)zirconium dichloride,
dimethylsilanediyl(3-methyl-cyclopentadienyl)(9-fluorenyl) zirconium dichloride,
dimethylsilanediyl(3-ethyl-cyclopentadienyl)(9-fluorenyl) zirconium dichloride,
1-2-ethane(3-tert-butyl-cyclopentadienyl)(9-fluorenyl)zirconium dichloride,
1-2-ethane(3-isopropyl-cyclopentadienyl)(9-fluorenyl)zirconium dichloride,
1-2-ethane(3-methyl-cyclopentadienyl)(9-fluorenyl)zirconium dichloride,
1-2-ethane(3-ethyl-cyclopentadienyl)(9-fluorenyl)zirconium dichloride,
dimethylsilandiylbis-6-(3-methylcyclopentadienyl-[1,2-b]-thiophene)zirconium dichloride;
dimethylsilandiylbis-6-(4-methylcyclopentadienyl-[1,2-b]-thiophene)zirconium dichloride;
dimethylsilandiylbis-6-(4-isopropylcyclopentadienyl-[1,2-b]-thiophene)zirconium dichloride;
dimethylsilandiylbis-6-(4-ter-butylcyclopentadienyl-[1,2-b]-thiophene)zirconium dichloride;
dimethylsilandiylbis-6-(3-isopropylcyclopentadienyl-[1,2-b]-thiophene)zirconium dichloride;
dimethylsilandiylbis-6-(3-phenylcyclopentadienyl-[1,2-b]-thiophene)zirconium dichloride;

dimethylsilandiylbis-6-(2,5-dimethyl-3-phenylcyclopenta-dienyl-[1,2-b]-thiophene)zirconium dichloride;
dimethylsilandiylbis-6-[2,5-dimethyl-3-(2-methylphenyl)cyclopentadienyl-[1,2-b]-thiophene]zirconium dichloride;
dimethylsilandiylbis-6-[2,5-dimethyl-3-(2,4,6-trimethylphenyl)cyclopentadienyl-[1,2-b]-thiophene]zirconium dichloride;
dimethylsilandiylbis-6-[2,5-dimethyl-3-mesitylenecyclopentadienyl-[1,2-b]-thiophene]zirconium dichloride;
dimethylsilandiylbis-6-(2,4,5-trimethyl-3-phenylcyclopentadienyl-[1,2-b]-thiophene)zirconium dichloride;
dimethylsilandiylbis-6-(2,5-diethyl-3-phenylcyclopentadienyl-[1,2-b]-thiophene)zirconium dichloride;
dimethylsilandiylbis-6-(2,5-diisopropyl-3-phenylcyclopentadienyl-[1,2-b]-thiophene)zirconium dichloride;
dimethylsilandiylbis-6-(2,5-diter-butyl-3-phenylcyclopentadienyl-[1,2-b]-thiophene)zirconium dichloride;
dimethylsilandiylbis-6-(2,5-ditrimetylsilyl-3-phenylcyclopentadienyl-[1,2-b]-thiophene)zirconium dichloride;
dimethylsilandiylbis-6-(3-methylcyclopentadienyl-[1,2-b]-silole)zirconium dichloride;
dimethylsilandiylbis-6-(3-isopropylcyclopentadienyl-[1,2-b]-silole)zirconium dichloride;
dimethylsilandiylbis-6-(3-phenylcyclopentadienyl-[1,2-b]-silole)zirconium dichloride;
dimethylsilandiylbis-6-(2,5-dimethyl-3-phenylcyclopentadienyl-[1,2-b]-silole)zirconium dichloride;
dimethylsilandiylbis-6-[2,5-dimethyl-3-(2-methylphenyl)cyclopentadienyl-[1,2-b]-silole]zirconium dichloride;
dimethylsilandiylbis-6-[2,5-dimethyl-3-(2,4,6-trimethylphenyl)cyclopentadienyl-[1,2-b]-silole]zirconium dichloride;
dimethylsilandiylbis-6-[2,5-dimethyl-3-mesitylenecyclopentadienyl-[1,2-b]-silole]zirconium dichloride;
dimethylsilandiylbis-6-(2,4,5-trimethyl-3-phenylcyclopentadienyl-[1,2-b]-silole)zirconium dichloride;
[dimethylsilyl(tert-butylamido)][(N-methyl-1,2-dihydrocyclopenta[2,1-b]indol-2-yl)]titanium dichloride;
[dimethylsilyl(tert-butylamido)][(6-methyl-N-methyl-1,2-dihydrocyclopenta[2,1-b]indol-2-yl)]titanium dichloride;
[dimethylsilyl(tert-butylamido)][(6-methoxy-N-methyl-1,2-dihydrocyclopenta[2,1-b]indol-2-yl)]titanium dichloride;
[dimethylsilyl(tert-butylamido)][(N-ethyl-1,2-dihydrocyclopenta[2,1-b]indol-2-yl)]titanium dichloride;
[dimethylsilyl(tert-butylamido)][(N-phenyl-1,2-dihydrocyclopenta[2,1-b]indol2-yl)]titanium dichloride;
[dimethylsilyl(tert-butylamido)][(6-methyl-N-phenyl-1,2-dihydrocyclopenta[2,1-b]indol2-yl)]titanium dichloride;
[dimethylsilyl(tert-butylamido)][(6-methoxy-N-phenyl-1,2-dihydrocyclopenta[2,1-b]indol2-yl)]titanium dichloride;
[dimethylsilyl(tert-butylamido)][(N-methyl-3,4-dimethyl-1,2-dihydrocyclopenta[2,1-b]indol-2-yl)]titanium dichloride;
[dimethylsilyl(tert-butylamido)][(N-ethyl-3,4-dimethyl-1,2-dihydrocyclopenta[2,1-b]indol-2-yl)]titanium dichloride;
[dimethylsilyl(tert-butylamido)][(N-phenyl-3,4-dimethyl-1,2-dihydroclopenta[2,1-b]indol-2-yl)]titanium dichloride;
as well as the correspondent titanium and hafnium compounds and the dibromide and diodide compounds.

The process according to the present invention shows several advantages with respect to the processes generally known in the state of the art. The overall yields starting from the ligands are generally higher than those reported in the art. Moreover, it is easier to purify the desired product, due to the better solubility of the formed intermediate alkylated metallocene with respect to the dihalide or monohalide product.

Further, because of the higher solubility of said intermediate metallocene it is also easy to separate the racemic and the meso form at this step and thus to obtain the substantially pure racemic or meso form as the final product.

The metallocene compounds obtained with the process according to the present invention, in combination with a suitable activator such as an alumoxane, or compound able to form alkylmetallocene cation can be used as a catalyst for the polymerization of olefins.

Particularly, they can be used for the homo or co-polymerization of alpha-olefins of formula $CH_2=CHR$ wherein R is hydrogen or a $C_1$-$C_{20}$ alkyl, such as propylene, 1-butene, 1-pentene, 4-methyl-1-pentene, 1-hexene and 1-octene.

An interesting use is for the production of isotactic, syndiotactic or atactic polypropylene.

Another interesting use is for the copolymerization of ethylene with alpha-olefins, such as propylene, 1-butene, 1-pentene, 4-methyl-1-pentene, 1-hexene and 1-octene, with cycloolefins, such as cyclopentene, cyclohexene, norbornene and 4,6-dimethyl-1-heptene, or with polyenes, such as 1,4-hexadiene, isoprene, 1,3-butadiene, 1,5-hexadiene and 1,6-heptadiene.

Further, they can be advantageously used in olefin oligomerization or hydrogenation reactions. The alumoxanes that can be used are considered to be linear, branched or cyclic compounds containing at least one group of the type:

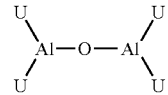

wherein the U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radicals, optionally containing silicon or germanium atoms, with the proviso that at least one U is different from halogen.

In particular, alumoxanes of the formula:

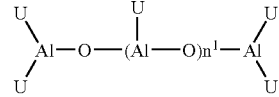

can be used in the case of linear compounds, wherein $n^1$ is 0 or an integer of from 1 to 40 and the substituents U are defined as above; or alumoxanes of the formula:

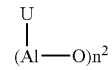

can be used in the case of cyclic compounds, wherein $n^2$ is an integer from 2 to 40 and the U substituents are defined as above.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and E⁻ is a compatible anion, which is able to stabilize the active catalytic species originating from the reaction of the two compounds, and which is sufficiently labile to be removed by an olefinic monomer. Preferably, the anion E⁻ comprises one or more boron atoms. More preferably, the anion E⁻ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910.

The catalyst component formed by contacting a metallocene compound and an alumoxane or a compound able to form an alkylmetallocene cation can suitably be used on inert supports, such as silica, alumina, styrene/divinylbenzene copolymers, polyethylene or polypropylene, particularly for use in the gas phase polymerizations.

The olefin polymerization processes can be carried out in liquid phase, optionally in the presence of an inert hydrocarbon solvent, either aromatic (e.g. toluene) or aliphatic (e.g. propane, hexane, heptane, isobutane, cyclohexane and 2,2,4-trimethylpentane). The polymerization temperature generally ranges from about 0° C. to about 250° C., and preferably from 20 to 150° C.

The following examples are given for illustrative and not limitative purposes.

General Procedures and Characterizations

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. $EtAlCl_2$ (Aldrich) and $AlCl_3$ (Aldrich) were used as received.

The proton spectra of ligands and metallocenes were obtained on a Bruker DPX 200 spectrometer operating in the Fourier transform mode at room temperature at 200.13 MHz. The samples were dissolved in $CD_2Cl_2$ (Aldrich, 99.5 atom % D) or 1,1,2,2-tetrachloroethane-$d_2$ (Acros, 99 atom % D). Preparation of the samples was carried out under nitrogen using standard inert atmosphere techniques. The residual peak of $CHDCl_2$ or $C_2HDCl_4$ in the $^1H$ spectra (5.35 ppm and 5.95 ppm, respectively) were used as a reference. Proton spectra were acquired with a 15° pulse and 2 seconds of delay between pulses; 32 transients were stored for each spectrum.

Dimethylsilanediyl [2-methyl-4-(4'-tert-butylphenyl)indenyl][2-isopropyl-4-(4'-tert-butylphenyl)indenyl)]dimethyl zirconium is prepared following the same procedure described in example 5 of PCT/EP02/14899 by using [2-methyl-4-(4'-tert-butylphenyl)indenyl][2-isopropyl-4-(4'-tert-butylphenyl)indenyl)]dimethylsilane instead of bis(2-methyl-indene)dimethylsilane.

Dimethylsilanediyl bis[2-methyl-(4,5-benzoindenyl)] dimethyl zirconium is prepared following the same procedure described in example 5 of PCT/EP02/14899 by using bis[2-methyl-(4,5-benzoindenyl)]dimethylsilane instead of bis(2-methyl-indenyl)dimethylsilane.

EXAMPLE 1

A 1.8 M solution of $EtAlCl_2$ in toluene (Aldrich, 6.3 mL, 11.34 mmol, Al/Zr=2.17/1) was added dropwise at room temperature under nitrogen atmosphere to a suspension of 3.8 g of dimethylsilanediyl [2-methyl-4-(4'-tert-butylphenyl)indenyl][2-isopropyl-4-(4'-tert-butylphenyl)indenyl)]dimethyl zirconium (MW=728.26, 5.22 mmol) in 20 mL of toluene in a 50 mL Schlenk flask. During the addition the colour turned from yellow to orange-red. The reaction mixture was then heated at 60° C. for 40 min: a $^1H$ NMR analysis in $CD_2Cl_2$ showed nearly quantitative conversion of the dimethyl complex into the dichloride complex (rac/meso 92/8). The final suspension was filtered at room temperature on a G4 frit: the residue was further washed with toluene and then dried under vacuo giving 3.90 g of an orange powder. The latter resulted to be dimethylsilanediyl [2-methyl-4-(4'-tert-butylphenyl)indenyl][2-isopropyl-4-(4'-tert-butylphenyl)indenyl)]zirconium dichloride (rac/meso 92/8) by $^1H$ NMR analysis in $CD_2Cl_2$: isolated yield 97.2%.

$^1H$ NMR ($CD_2Cl_2$, δ, ppm): 1.07 (d, 3H, J=6.85 Hz, $CH_3$, rac); 1.15 (d, 3H, J=6.85 Hz, $CH_3$, rac); 1.22 (d, 3H, J=6.85 Hz, $CH_3$, meso); 1.32 (s, 3H, $Me_2Si$, meso); 1.37, 1.38 (s, 36H, t-Bu, rac and meso); 1.39, 1.40 (s, 6H, $Me_2Si$, rac); 1.48 (d, 3H, J=6.85 Hz, $CH_3$, meso); 1.54 (s, 3H, $Me_2Si$, meso); 2.28 (s, 3H, 2-$CH_3$, rac); 2.41 (s, 3H, 2-$CH_3$, meso); 3.18-3.38 (m, 2H, J=6.85 Hz, CH, rac and meso); 6.86-7.75 (m, 32H, Cp-H and Ar, rac and meso).

COMPARATIVE EXAMPLE 1

Aluminum chloride (Aldrich, 99.9%, 0.18 g, MW=133.34, 1.35 mmol, Al/Zr=2.50/1) was slowly added at room temperature under nitrogen atmosphere to a suspension of 0.39 g of dimethylsilanediyl [2-methyl-4-(4'-tert-butylphenyl)indenyl][2-isopropyl-4-(4'-tert-butylphenyl)indenyl)]dimethyl zirconium (MW=728.26, 0.54 mmol) in 10 mL of toluene in a 100 mL Schlenk flask. The reaction mixture was heated at 40° C. for 2 h: a $^1H$ NMR analysis in $CD_2Cl_2$ showed conversion of the dimethyl complex into the dichloride complex (rac/meso 56/44), impure of by-products not yet identified. The final suspension was added of 60 mL of toluene, heated at 60° C., stirred for 15 min at this temperature and filtered on a G4 frit. The residue was discarded, whereas the filtrate was dried in vacuo and subsequently treated with ethyl ether. The resulting suspension was stirred at room temperature for 15 min and then filtered on a G4 frit: the residue was dried under vacuo giving 0.31 g of an orange powder. The latter resulted to be dimethylsilanediyl [2-methyl-4-(4'-tert-butylphenyl)indenyl][2-isopropyl-4-(4'-tert-butylphenyl)indenyl)]zirconium dichloride (rac/meso 56/44) by $^1H$ NMR analysis in $CD_2Cl_2$: isolated yield 74.7%.

EXAMPLE 2

A 1.8 M solution of EtAlCl$_2$ in toluene (Aldrich, 0.85 mL, 1.53 mmol, Al/Zr=2.16/1) was added dropwise at room temperature under nitrogen atmosphere to a suspension of 0.38 g of dimethylsilanediyl bis[2-methyl-(4,5-benzoindenyl)]dimethyl zirconium (MW=535.92, 0.71 mmol) in 15 mL of toluene in a 50 mL Schlenk flask. The reaction mixture was stirred at room temperature for 1 h: a $^1$H NMR analysis in CD$_2$Cl$_2$ showed nearly quantitative conversion of the dimethyl complex into the dichloride complex. The final suspension was filtered at room temperature on a G4 frit: the residue was further washed with toluene and then dried under vacuo giving 0.38 g of a yellow powder. The latter resulted to be dimethylsilanediyl bis[(2-methyl-(4,5-benzoindenyl)]zirconium dichloride rac/meso 28/72) by $^1$H NMR analysis in CD$_2$Cl$_2$: isolated yield 92.8%.

$^1$H NMR (CD$_2$Cl$_2$, δ, ppm): 1.30 (s, 3H, Me$_2$Si, meso); 1.39 (s, 6H, Me$_2$Si, rac); 1.50 (s, 3H, Me$_2$Si, meso); 2.39 (s, 6H, 2-CH$_3$, rac); 2.58 (s, 6H, 2-CH$_3$, meso); 7.14-8.00 (m, 28H, Cp-H and Ar, rac and meso).

COMPARATIVE EXAMPLE 2

Aluminum chloride (Aldrich, 99.9%, 0.27 g, MW=133.34, 2.02 mmol, Al/Zr=2.77/1) was slowly added at room temperature under nitrogen atmosphere to a suspension of 0.39 g of dimethylsilanediyl bis[2-methyl-(4,5-benzoindenyl)]dimethyl zirconium (MW=535.92, 0.73 mmol) in 15 mL of toluene in a 150 mL Schlenk flask. The reaction mixture was stirred at room temperature for 1 h: a $^1$H NMR analysis in CD$_2$Cl$_2$ showed conversion of the dimethyl complex into the dichloride complex (rac/meso 26/74), impure of by-products not yet identified. The final suspension was added of 80 mL of toluene, heated at 60° C., stirred for 30 min at this temperature and filtered on a G4 frit. The filtrate was discarded, whereas the residue was further extract with toluene and dried in vacuo. The extract was subsequently treated with 20 mL of ethyl ether. The resulting suspension was stirred at room temperature for 20 min and then filtered on a G4 frit: the residue was dried under vacuo giving 0.34 g of a yellow powder. The latter resulted to be dimethylsilanediyl bis[(2-methyl-(4,5-benzoindenyl)]zirconium dichloride (rac/meso 29/71) by $^1$H NMR analysis in CD$_2$Cl$_2$: isolated yield 80.9%.

EXAMPLE 3

"One Pot" Synthesis

A 3.05 M MeLi solution in diethoxymethane (Chemetall, 11.2 mL, 34.16 mmol, MeLi:ligand=2.08:1) was added dropwise at room temperature under nitrogen atmosphere to a solution of 10.00 g of [2-methyl-4-(4'-tert- butylphenyl)indenyl] [2-isopropyl-4-(4'-tert-butylphenyl)indenyl)]dimethylsilane (98.6% pure by GC-MS, MW=608.98, 16.42 mmol) in 60 mL of THF in a 500 mL reactor. At the end of the addition, the reaction mixture was stirred for 2 h with final formation of an orange-red solution. After about 1 hour additional 11.2 mL of a 3.05 M MeLi solution in diethoxymethane (34.16 mmol, MeLi:ligand=2.08:1) were then quickly added at room temperature to the dilithium salt of the ligand. At the same time anhydrous THF (60 mL) was slowly added at −20° C. under nitrogen atmosphere to 3.82 g of ZrCl$_4$ (Aldrich, MW 233.03, 16.39 mmol, ZrCl$_4$:ligand=1/1) in a 250 mL Schlenk flask. At the end of the addition, the slurry containing ZrCl$_4$(THF)$_2$ was allowed to warm up to room temperature and stirred for 1 h. Then the ZrCl$_4$(THF)$_2$ slurry was slowly added at room temperature to the ligands solution containing a 2-fold MeLi excess. The resulting reaction mixture was heated at 65° C. and stirred for 12 h at this temperature. A $^1$H NMR analysis in CD$_2$Cl$_2$ showed nearly quantitative conversion of the starting ligand to the dimethyl complex. The reaction mixture was then concentrated in vacuum up to 10% of the total volume (ca. 15 mL); pentane (ca. 50 mL) was added and the resulting suspension stirred for 15 min at room temperature. Then it was filtered on a G4 frit, equipped with a mechanical stirrer to allow a continuous and effective stirring of the crude mixture. The residue on the frit was washed once with pentane (50 mL), while the filtrates were discarded. The residue on the frit was treated at 60° C. unders stirring with about 300 mL of toluene and then filtrated again on a G4 frit to separate the dimethyl complex (as filtrate). A 1.8 M solution of EtAlCl$_2$ in toluene (Aldrich, 6.5 mL, 11.7 mmol, Al/Zr=0.71/1) was added dropwise at room temperature to the above solution. The reaction mixture was heated at 65° C. for 1 h: a $^1$H NMR analysis in CD$_2$Cl$_2$ showed nearly quantitative conversion of the dimethyl complex into the dichloride complex. The orange-red suspension was concentrated up to 10% of the total volume (ca. 30 mL) and filtered at room temperature on a G4 frit, equipped with a mechanical stirrer to allow a continuous and effective stirring of the crude mixture. The residue on the frit was washed once with toluene and then dried under vacuo giving an orange powder. The latter resulted to be rac/meso mixtures of [2-methyl-4-(4'-tert-butylphenyl)indenyl][2-isopropyl-4-(4'-tert-butylphenyl)indenyl)]zirconium dichloride by $^1$H NMR analysis in CD$_2$Cl$_2$: isolated yield 62.5% based on Zr.

An additional $^1$H NMR analysis of the final powder was done in 1,1,2,2-tetrachloroethane-d$^2$ to have a sample fully soluble in the NMR solvent.

$^1$H NMR (C$_2$D$_2$Cl$_4$, δ, ppm) rac isomer: 0.99 (d, 3H, J=6.46 Hz, CH$_3$); 1.09 (d, 3H, J=6.46 Hz, CH$_3$); 1.30 (s, 18H, t-Bu); 1.31 (bs, 6H, Me$_2$Si); 2.22 (s, 3H, 2-CH$_3$); 3.23 (m, 1H, J=6.46 Hz, CH); 6.96 (d, 2H, J=8.41 Hz, CH); 7.07 (t, 2H, J=7.83 Hz, CH); 7.28-7.64 (m, 12H, CH).

The invention claimed is:
1. A process for preparing halide metallocene compounds of formula (I):

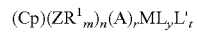

$$(Cp)(ZR^1{}_m)_n(A)_rML_yL'_t \qquad (I)$$

wherein
  $(ZR^1{}_m)_n$ is a divalent group bridging said Cp and said A moieties;
  Z is selected from C, Si, Ge, N or P;
  R$^1$ is equal to or different from each other, and is selected from hydrogen, a linear or branched, saturated or unsaturated C$_1$-C$_{20}$ alkyl, C$_3$-C$_{20}$ cycloalkyl, C$_6$-C$_{20}$ aryl, C$_7$-C$_{20}$ alkylaryl, and C$_7$-C$_{20}$ arylalkyl, said R$^1$ optionally contains one or more heteroatoms belonging to groups 13-17 of the Periodic Table of the Elements, and said R$^1$ can be an aliphatic or aromatic C$_4$-C$_7$ ring optionally substituted;
  Cp is an unsubstituted or substituted cyclopentadienyl, optionally condensed to one or more unsubstituted, substituted, saturated, unsaturated, or aromatic rings comprising 4 to 6 carbon atoms, said Cp optionally contains one or more heteroatoms belonging to groups 13-17 of the Periodic Table of the Elements;

A is selected from O, S, $NR^2$, and $PR^2$;

$R^2$ is selected from hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl, or said $R^2$ can be Cp;

M is selected from zirconium, titanium, and hafnium;

L is equal to or different from each other, and is selected from chlorine, bromine, iodine;

L' is selected from hydrogen, or a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl, said L' optionally contains one or more Si or Ge atoms;

m is 1 or 2, wherein when Z is N or P m is 1, and when Z is C, Si, or Ge m is 2;

n is 0, 1, 2, 3 or 4, wherein when r is 0 or 2 n is 0;

r is 0, 1 or 2;

y is 1, 2, or 3; and t is 0, 1 or 2, wherein (y+t) is equal to an oxidation state of M−(1+r);

said process comprising contacting a compound of formula (II):

$$(Cp)(ZR^1{}_m)_n(A)_rML'_p \qquad (II)$$

wherein

Cp, Z, $R^1$, A, M, L', m, r, and n are defined above; and p is said oxidation state M−(1+r);

with at least p minus t equivalents with respect to the metal M of the compound of formula (II) of an halogenating agent of formula (III):

$$R^3{}_xTL_w \qquad (III)$$

wherein:

L is defined above;

$R^3$ is selected from hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl;

T is a metal of groups 2-14 of the Periodic Table of the Elements;

x is ≧1; and w is ≧1, wherein (x+w) is equal to an oxidation state of T.

2. The process according to claim 1, wherein $R^3$ is selected from methyl, ethyl, n-propyl, isopropyl, n-butyl, isobutyl, phenyl or benzyl;

T is selected from a metal from groups 11-14 of the Periodic Table of the Elements; and x is 1.

3. The process according to claim 1, wherein T is selected from aluminium, zinc, tin, germanium, and copper.

4. The process according to claim 1, wherein

L is chlorine;

L' is selected from methyl, ethyl, n-butyl, sec-butyl, phenyl, benzyl, and —$CH_2Si(CH_3)_3$;

r is 1;

y is 2; and t is 0.

5. A process for preparing halide metallocene compounds of formula (I):

$$(Cp)(ZR^1{}_m)_n(A)_rML_yL'_t \qquad (I)$$

wherein

Cp is an unsubstituted or substituted cyclopentadienyl, optionally condensed to one or more unsubstituted, substituted, saturated, unsaturated, or aromatic rings comprising 4 to 6 carbon atoms, said Cp optionally contains one or more heteroatoms belonging to groups 13-17 of the Periodic Table of the Elements;

Z is selected from C, Si, Ge, N or P;

$R^1$ is equal to or different from each other, and is selected from hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl, said $R^1$ optionally contains one or more heteroatoms belonging to groups 13-17 of the Periodic Table of the Elements, and said $R^1$ can be an aliphatic or aromatic $C_4$-$C_7$ ring optionally substituted;

m is 1 or 2, wherein when Z is N or P m is 1, and when Z is C, Si, or Ge m is 2;

n is 0, 1, 2, 3 or 4, wherein when r is 0 or 2 n is 0;

A is selected from O, S, $NR^2$, and $PR^2$;

r is 0, 1 or 2;

M is selected from zirconium, titanium, and hafnium;

L is equal to or different from each other, and is selected from chlorine, bromine, iodine;

L' is selected from hydrogen, or a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl, said L' optionally contains one or more Si or Ge atoms;

t is 0, 1 or 2, wherein (y+t) is equal to an oxidation state of M−(1+r); and y is 1, 2, or 3;

comprising:

reacting a ligand of formula $(Y-Cp)(ZR^1{}_m)_n(A-Y)_r$, or when n is 0, a mixture of ligands comprising Y-Cp and r(A-Y) with an amount EQ of a compound of formula $L'_jB$ or L'MgL''' to obtain an intermediate product such that EQ≧1+r molar equivalents with respect to Cp, wherein Cp, A, Z, $R^1$, m, n, r, and L' are defined above;

L''' is selected from the group consisting of chlorine, bromine, and iodine;

Y is the same or different from each other, and is a suitable leaving group;

Mg is magnesium;

B is selected from an alkaline and alkaline-earth metal; and j is 1 or 2, wherein when B is an alkali metal j is 1, and when B is an alkaline-earth metal j is 2;

reacting said intermediate product with at least 1 molar equivalent with respect to Cp of a compound of formula $ML''_4$ to obtain a mixture of meso and rac metallocene intermediates, wherein M is defined above; and L'' is selected from the group consisting of chlorine, bromine, and iodine;

optionally purifying said mixture of meso and rac metallocene intermediates and separating said meso and said rac metallocene intermediates; and reacting said mixture with at least y equivalents, wherein y is defined above, of an halogenating agent of formula (III):

$$R^3{}_xTL_w \qquad (III)$$

wherein

R³ is selected from hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl, and $C_7$-$C_{20}$ arylalkyl;

T is a metal of groups 2-14 of the Periodic Table of the Elements;

L is defined above;

x is $\geq 1$; and w is $\geq 1$, wherein (x+w) is equal to an oxidation state of T.

6. The process according to claim 5, wherein said amount EQ of a compound of formula L'$_j$B or L'MgL''' is such that 1+r$\leq$EQ$\leq$4+r.

7. The process according to claim 5, wherein said ligand of formula (Y-Cp)(ZR¹$_m$)$_n$(A-Y)$_r$, or when n is 0, a mixture of ligands comprising said ligands Y-Cp and r(A-Y) is reacted with an amount EQ of a compound of formula L'$_j$B or L'MgL''' such that EQ is about 1+r molar equivalents with respect to Cp at a temperature from −10° C. to 70° C.

8. The process according to claim 7, further comprising adding an amount EQ of a compound of formula L'$_j$B or L'MgL''' such that 1+r$\leq$EQ$\leq$2+r.

9. The process according to claim 5, wherein said intermediate product is heated at a temperature between 0° C. and 80° C.; adding compound ML''$_4$ to said intermediate product to form a reaction mixture, wherein said intermediate product is a solution or a slurry; reacting said reaction mixture for 10 minutes to 36 hours.

10. The process according to claim 1, further comprising adding said halogenating agent of formula (III) to formula (II) at a temperature range from −50° C. to +150° C.

11. The process according to claim 5, wherein said halogenating agent of formula (III) is added dropwise at a temperature ranging from −50° C. to +150° C., further comprising reacting a mixture of formula (II) and formula (III) under stirring for a period from 1 to 6 hours and at a temperature from −10° C. to +80° C.

12. The process according to claim 5, wherein said compound of formula (I) has formula (IV)

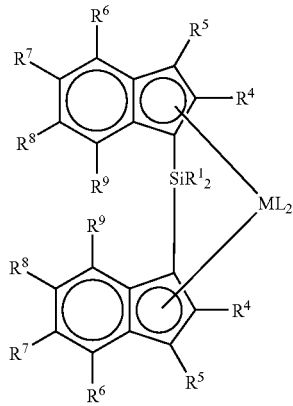

(IV)

wherein:

M, L and R¹ are defined in claim 5;

R⁴ is equal to or different from each other, and is selected from a hydrogen, a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, and $C_7$-$C_{20}$-arylalkyl radical, said R⁴ optionally contains heteroatoms belonging to groups 13-17 of the Periodic Table of the Elements;

R⁵, R⁶, R⁷, R⁸ and R⁹ are equal to or different from each other, and are selected from hydrogen, a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, and $C_7$-$C_{20}$-arylalkyl radicals, said R⁵, R⁶, R⁷, R⁸ and R⁹ optionally contain heteroatoms belonging to groups 13-17 of the Periodic Table of the Elements, wherein two vicinal R⁵, R⁶, R⁷, R⁸ and R⁹ can optionally form one or more condensed 5 or 6 membered saturated or unsaturated rings optionally containing heteroatoms belonging to groups 13-16 of the Periodic Table of the Elements, said rings are optionally substituted with at least one $C_1$-$C_{40}$ alkyl.

13. The process according to claim 12 wherein

R⁴ is selected from methyl, ethyl, and isopropyl radicals; and

R⁶ is selected from a $C_1$-$C_{20}$-alkyl, a $C_6$-$C_{20}$-aryl, and a $C_7$-$C_{20}$-arylalkyl radical.

* * * * *